United States Patent [19]

Fauver et al.

[11] Patent Number: 5,386,069
[45] Date of Patent: Jan. 31, 1995

[54] PROCESS FOR PREPARATION OF DIFLUORO-TETRAIODOBENZENE

[75] Inventors: Jerry S. Fauver; David R. Fagerburg, both of Kingsport, Tenn.

[73] Assignee: Eastman Chemical Company, Kingsport, Tenn.

[21] Appl. No.: 113,466

[22] Filed: Aug. 30, 1993

Related U.S. Application Data

[63] Continuation-in-part of Ser. No. 57,926, May 7, 1993, abandoned.

[51] Int. Cl.$^6$ .............................................. C07C 25/13
[52] U.S. Cl. ................................................... 570/147
[58] Field of Search ............................. 570/147, 206

[56] References Cited

U.S. PATENT DOCUMENTS

| | | | |
|---|---|---|---|
| 4,716,254 | 12/1987 | Cobb | 570/147 |
| 4,778,939 | 10/1988 | Tustin et al. | 570/206 |
| 4,778,940 | 10/1988 | Rule et al. | 570/206 |
| 5,015,792 | 5/1991 | Nunn | 570/206 |

OTHER PUBLICATIONS

J. Macromol. Sci.-Chem., A28 (11 & 12) (1991).

*Primary Examiner*—Alan Siegel
*Attorney, Agent, or Firm*—Charles R. Martin

[57] ABSTRACT

Disclosed is a process for preparation of difluoro-tetraiodobenzene comprising contacting difluorobenzene with molecular iodine in the presence of fuming sulfuric acid.

2 Claims, No Drawings

PROCESS FOR PREPARATION OF DIFLUORO-TETRAIODOBENZENE

This application is a continuation-in-part of application Ser. No. 08/057,926 filed May 7, 1993 now abandoned.

This invention pertains to a process for preparation of difluoro-tetraiodobenzene.

Tetraiodo aromatic compounds are valuable compounds having a variety of uses. For example, it is known these compounds can be carbonylated in the presence of diamines in an appropriate solvent to produce a high molecular weight polyimide.

We have now discovered a process for the preparation of difluoro-tetraiodobenzene. The process we have discovered is particularly desirable because essentially no side products are produced.

Broadly, the process of our invention can be described as a process for preparation of difluoro-tetraiodobenzene comprising contacting difluorobenzene with molecular iodine in the presence of fuming sulfuric acid.

The difluorobenzene useful in the process of this invention can comprise either the 1,2 or the 1,3 or the 1,4 isomer. Preferable the 1,4 isomer is used. These compounds and methods for their preparation are well known in the art.

In the process of this invention the difluoro compound is reacted with molecular iodine in the presence of fuming sulfuric acid. The $SO_3$ content of the fuming sulfuric acid is in the range of 5 to 50 weight percent, preferably in the range of 20 to 35 weight percent, based on the weight of the sulfuric acid.

The iodine useful in the process of this invention is molecular iodine, often identified as $I_2$.

The moles of iodine compared to the moles of difluorobenzene can vary widely and are broadly in the range of 20:1 to 1:20. If a molar excess of iodine is used there will be iodine remaining after the reaction is complete and the iodine must be removed from the zone in which the reaction occurred. If a molar deficiency of iodine is used there will be unreacted difluorobenzene remaining in the reaction zone. Preferably, the molar ratio of iodine to difluorobenzene is in the range of 3:1 to 1:1 and most preferably, the molar ratio is in the range of 2.5:1 to 1.5:1.

The time and temperature of the reaction can be varied over a wide range. In order to practice the invention in a commercially acceptable manner the temperature should be between the melting point and boiling points of the difluorobenzene. For example, the melting point of 1,4-difluorobenzene is −13° C. and the boiling point is 89° C. so when the preferred embodiment of the invention is practiced with 1,4-difluorobenzene the temperature should be within the range of −13° C. to 89° C. Preferably, the reaction is conducted at a temperature greater than 25° C. More preferably the temperature is in the range of 0° C. to 85° C. and most preferably the temperature is in the range of room temperature to 80° C. The reaction time must be sufficient to permit formation of the difluoro-tetrabenzene and is a function of temperature. Generally, at least 1 minute is required at higher temperatures and at least 5 minutes at lower temperatures.

The process of this invention can be practiced either as a batch process or continuously. When the process is practiced as a batch process a conventional commercial stirred reactor can be used.

The compound prepared by the process of this invention can be broadly described as a difluoro-tetraiodobenzene. The positions of the fluorine atoms on the starting difluorobenzene determines the positions of the fluorine atoms on the difluoro-tetraiodobenzene because the positions of the fluorine atoms do not change on the ring during the reaction. For example, if the preferred embodiment of the invention is practiced and the starting material is 1,4-difluorobenzene the final compound will be 1,4-difluoro-tetraiodobenzene. Similarly, if the invention is practiced using 1,3-difluorobenzene as the starting material the final compound will be 1,3-difluoro-tetraiodobenzene.

The compounds prepared by the process of this invention are useful in preparation of high molecular weight polyimides which can be used to prepare films. In one embodiment wherein the compound is 1,4-difluoro-2,3,5,6-tetraiodobenzene a high molecular weight polyimide can be formed by reacting this compound with 5-amino-3-(4-aminophenyl)-1,1,3-trimethylindane in accordance with the method disclosed on page 1218 of *J. Macromol. Sci.—Chem.*, A28(11 & 12) (1991). In this reaction these compounds are reacted, for example, in N,N-dimethyl acetamide at 115° C. under 95 psi CO in the presence of 6% bis(triphenylphosphine) palladium (II) chloride] and 12% triphenyl phosphine with later addition of 1,8-diazobicyclo [5.4.0] undec-7-ene in the amount of 4 times the molar amount of triphenyl phosphine, to form a high molecular weight polyimide in accordance with the following reaction.

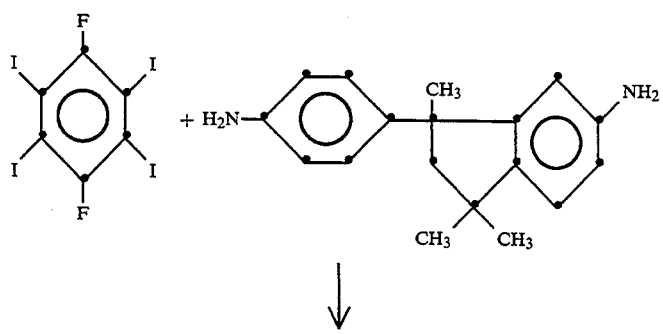

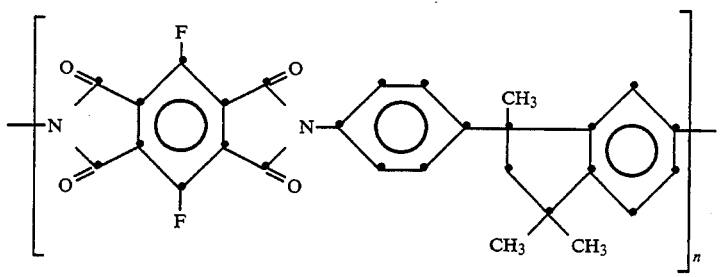

After 24 hours the reaction mixture was moderately vicous. The polymer solution was filtered and precipitated twice into methanol and dried. The inherent viscosity was 0.56 as measured as a 0.25 wt % solution in N,N-dimethylacetamide and the molecular weight was about 280,000. The polymer was cast on glass as a N,N-dimethylacetamide solution. After drying overnight at 100° C. a dark film had formed. The film was removed and examined. The film was found to be a tough, flexible film which had mechanical properties suitable for packaging or high temperature insulation.

EXAMPLE 1

This example illustrates the preparation of 1,4-difluoro-2,3,5,6-tetraiodobenzene according to the process of this invention.

Iodine, 1100 g ($I_2$, 4.334 mol) and 1300 ml fuming sulfuric acid (27–33% $SO_3$) were added to a 3 liter, 3 neck round bottom flask fitted with a water jacketed condenser. The mixture was stirred for 1 hour at room temperature. Then 400 g (3.506 mol, $I_2$ to 1,4-difluorobenzene ratio=1.24) of 1,4-difluorobenzene was added slowly using an addition funnel equipped with a needle valve over approximately 30 min at room temperature. Product crystals were observed forming with each drop of added 1,4-difluorobenzene. The mixture was then placed on the steam bath for 6 hours with stirring. The mixture was allowed to stand at room temperature over night and poured over crushed ice in an aqueous sodium bisulfite solution. The solution was filtered and 975 g of solids was recovered. The yield was 69% based on $I_2$ moles. Analysis by gas chromatography shows the solids to be approximately 95% 1,4-difluoro-2,3,5,6-tetraiodobenzene and the remaining approximately 5% to be 1,4-difluoro 2,5,6-triiodobenzene.

EXAMPLE 2

This example also illustrates preparation of 1,4-difluoro-2,3,5,6-tetraiodobenzene according to the process of this invention.

$I_2$, 550 g (2,167 mol) and 1300 Ml fuming sulfuric acid (27–33% $SO_3$) were added to a 3 liter, 3 neck round bottom flask and stirred at room temperature for one hour. Then 400 g (3.506 mol, $I_2$ to difluorobenzene ratio=0.62) of 1,4-difluorobenzene was added slowly using an addition funnel equipped with a needle valve to meter flow over a period of approximately 50 min. at room temperature. The mixture was then placed on the steam bath for approximately 3.5 hr. The mixture was cooled to near room temperature and poured into the aqueous sodium bisulfite crushed ice solution. Filtration recovered 629.7 g and the yield was 89% based on $I_2$. Analysis by gas chromatography shows the solids to be approximately 95% 1,4-difluoro-2,3,5,6-tetraiodobenzene and the remaining approximately 5% to be 1,4-difluoro 2,5,6-triiodobenzene.

EXAMPLE 3

This example illustrates that the process of the invention does not produce a tetraiodo product in usable quantities and purity when a dichlorobenzene is employed instead of a difluorobenzene.

Iodine, 137.5 g (0.542 mol) and 325 ml fuming sulfuric acid (27–33% $SO_3$) were added to a 3 liter, 3 neck round bottom flask fitted with a jacketed condenser. The mixture was stirred at room temperature for one hour. 100 g (0.68 mol, iodine to dichlorobenzene ratio=0.797) of p-dichlorobenzene was melted on the steam bath and poured into an addition funnel equipped with a needle valve. The melted p-dichlorobenzene was added drop wise over approximately 15 min. The mixture was placed on the steam bath for about 4 hr with stirring. The mixture was then cooled to room temperature and poured into the crushed ice and sodium bisulfite solution. The solids were filtered and 152.83 g were recovered. Analysis revealed the following compounds: 1,4-dichloro-2,5-diiodobenzene (A); 1,2,4,5,-tetrachloro-3,6-diiodobenzene (B); 1,4-dichloro-2,3,5-triiodobenzene (C); 1,2,4-trichloro-3,5,6-triiodobenzene (D); and 1,4-dichloro-2,3,5,6-tetraiodobenzene (E). The major product was compound (C). Compounds (B) and (D) were present in significant quantity and only a small amount of (A) and the desired product (E) were present. Thus, not only was a tetraiodinated product not obtained in high yield also halogen exchange was observed which resulted in the original 1,4 pattern of halogen substitution not being retained in some of the final products.

EXAMPLE 4

This example further illustrates that the process of the invention does not produce a tetraiodo product in usable quantities and purity when a dibromobenzene is employed instead of a difluorobenzene.

Iodine, 90 g (0,354 mol) and 325 ml fuming sulfuric acid (27–33% $SO_3$) were added to a 2 liter, 3 neck round bottom flask fitted with a jacketed condenser. The mixture was stirred at room temperature for approximately one hour. Then 100 g of p-dibromobenzene crystals (0.424 mol, iodine to dibromobenzene ratio=0.835) were added to the reaction through the condenser a few grams at a time over a period of 12 min. The mixture was then placed on the steam bath with the stirring for 4.5 hr. The mixture was allowed to stand over night at room temperature and poured into the aqueous sodium bisulfite solution and crushed ice. Filtration recovered 256.17 g of crude solids. Analysis revealed the major products to be isomers of dibromo-diiodobenzene with only a very small amount of the desired 1,4-dibromo-2,3,5,6-tetraiodobenzene present. There were 6 other iodinated compounds containing less than 4 iodines per molecule also present in a higher amount than the desired product. Additionally, some tribromo-products were also detected. Thus, not only was a tetraiodinated product not obtained in high yield also halogen exchange was observed which resulted in the original 1,4 pattern of halogen substitution not being retained in some of the final products.

We claim:

1. A process for preparation of difluoro-tetraiodobenzene comprising contacting difluorobenzene with molecular iodine in the presence of fuming sulfuric acid.

2. A process for preparation of 1,4-difluoro-2,3,5,6-tetraiodobenzene comprising contacting 1,4-difluorobenzene with molecular iodine in the presence of fuming sulfuric acid at a temperature greater than 25° C.

* * * * *